(12) United States Patent
Ioachim

(10) Patent No.: US 10,466,041 B2
(45) Date of Patent: Nov. 5, 2019

(54) REFERENCE SYSTEM FOR ONLINE VISION INSPECTION

(71) Applicant: BOMBARDIER INC., Dorval (CA)

(72) Inventor: Octavian Ioachim, Pointe-Claire (CA)

(73) Assignee: BOMBARDIER INC., Dorval (CA)

( * ) Notice: Subject to any disclaimer, the term of this patent is extended or adjusted under 35 U.S.C. 154(b) by 169 days.

(21) Appl. No.: 15/538,449

(22) PCT Filed: Dec. 17, 2015

(86) PCT No.: PCT/IB2015/059748
§ 371 (c)(1),
(2) Date: Jun. 21, 2017

(87) PCT Pub. No.: WO2016/103125
PCT Pub. Date: Jun. 30, 2016

(65) Prior Publication Data
US 2019/0101383 A1 Apr. 4, 2019

Related U.S. Application Data

(60) Provisional application No. 62/095,661, filed on Dec. 22, 2014.

(51) Int. Cl.
*G06K 9/00* (2006.01)
*G01B 11/25* (2006.01)
(Continued)

(52) U.S. Cl.
CPC .......... *G01B 11/2513* (2013.01); *B29C 70/30* (2013.01); *G01N 21/8806* (2013.01)

(58) Field of Classification Search
CPC ..... B29C 64/386; B29C 64/393; B33Y 10/00; B33Y 50/02; G05B 19/4099; G05B 2219/35134; G05B 2219/49007
See application file for complete search history.

(56) References Cited

U.S. PATENT DOCUMENTS

| 4,703,648 A | 11/1987 | Baresh |
| 5,000,037 A | 3/1991 | Baresh |

(Continued)

FOREIGN PATENT DOCUMENTS

| DE | 19536294 | 4/1997 |
| EP | 2273229 | 1/2011 |

(Continued)

OTHER PUBLICATIONS

Uhart et al., "Improving Accuracy in Robotised Fiber Placement Using Force and Visual Servoing External Hybrid control Scheme", Sep. 2014, pp. 1-44.

(Continued)

*Primary Examiner* — Bhavesh M Mehta
*Assistant Examiner* — Ian L Lemieux
(74) *Attorney, Agent, or Firm* — Norton Rose Fulbright Canada LLP

(57) ABSTRACT

There is described a method for referencing a composite structure within an online vision inspection system. Referencing is performed independently from a positioning accuracy of an automated tool with which the composite structure is manufactured. Reference targets provided on a contour of a lay-up surface are used to correlate an image reference system with a mold reference system.

31 Claims, 13 Drawing Sheets

(51) Int. Cl.
    *B29C 70/30*   (2006.01)
    *G01N 21/88*   (2006.01)

(56) References Cited

U.S. PATENT DOCUMENTS

| | | | |
|---|---|---|---|
| 6,041,132 | A | 3/2000 | Isaacs et al. |
| 6,990,215 | B1 | 1/2006 | Brown et al. |
| 7,193,696 | B2 | 3/2007 | Engelbart et al. |
| 7,307,737 | B1 | 12/2007 | Kling, III et al. |
| 7,555,404 | B2 | 6/2009 | Brennan et al. |
| 7,835,567 | B2 | 11/2010 | Oldani |
| 7,978,328 | B2 | 7/2011 | Engelbart et al. |
| 8,840,742 | B2 | 5/2014 | Pham et al. |
| 8,723,458 | B1 | 6/2014 | Engelbart et al. |
| 2008/0006102 | A1 | 1/2008 | Engelbart et al. |
| 2010/0112190 | A1 | 5/2010 | Drewett et al. |
| 2011/0089591 | A1 | 4/2011 | Gordon et al. |
| 2014/0081444 | A1 | 3/2014 | Rudberg et al. |
| 2014/0147971 | A1* | 5/2014 | Yokosawa ......... H01L 21/67294 438/107 |
| 2014/0148939 | A1* | 5/2014 | Nakano ............ G01B 11/2545 700/166 |
| 2015/0022826 | A1* | 1/2015 | Cramer .................. G01S 17/66 356/620 |
| 2015/0177158 | A1* | 6/2015 | Cheverton ......... G01N 15/0227 700/119 |

FOREIGN PATENT DOCUMENTS

| | | |
|---|---|---|
| FR | 2932429 | 12/2009 |
| WO | WO0188471 | 11/2001 |

OTHER PUBLICATIONS

Siqi Zhu, "An Automated Fabric Layup Machine for the Manufacturing of Fiber Reinforced Polymer Composite", Graduate Theses and Dissertations, Iowa State University, 2013.

International Search Repot and Written Opinion issued in PCT application No. PCT/IB2015/059748.

* cited by examiner

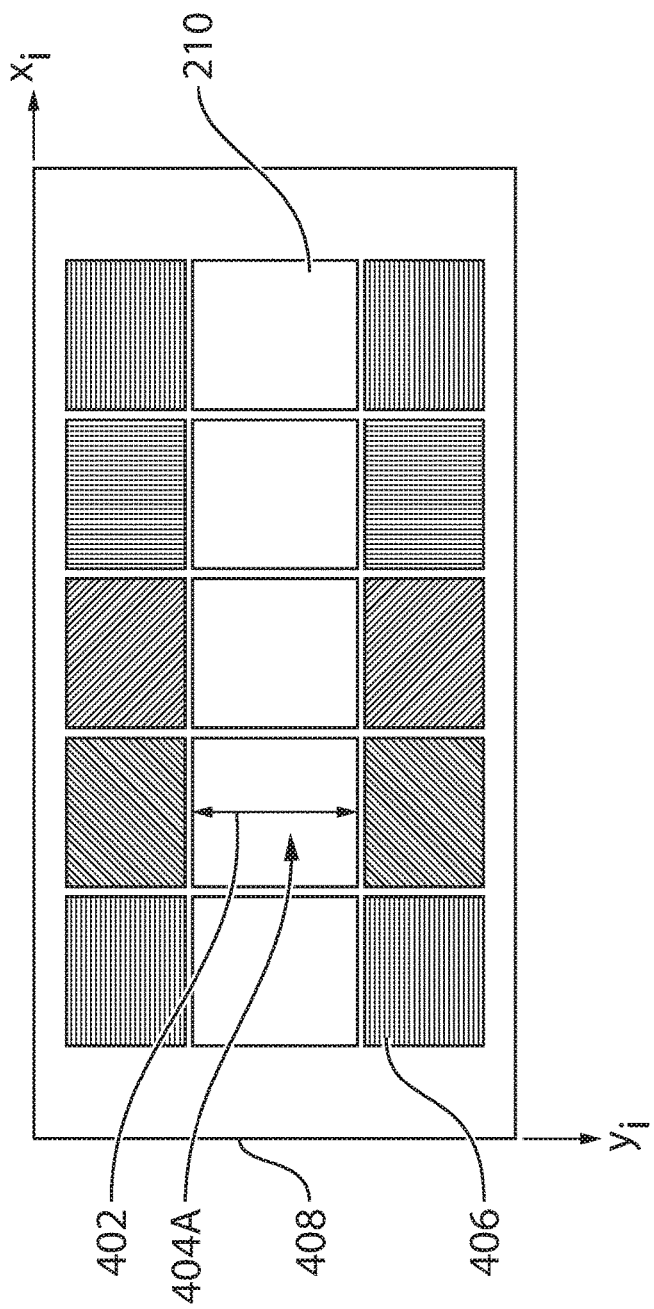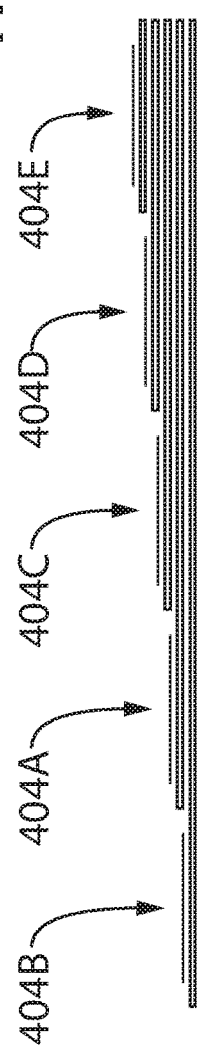

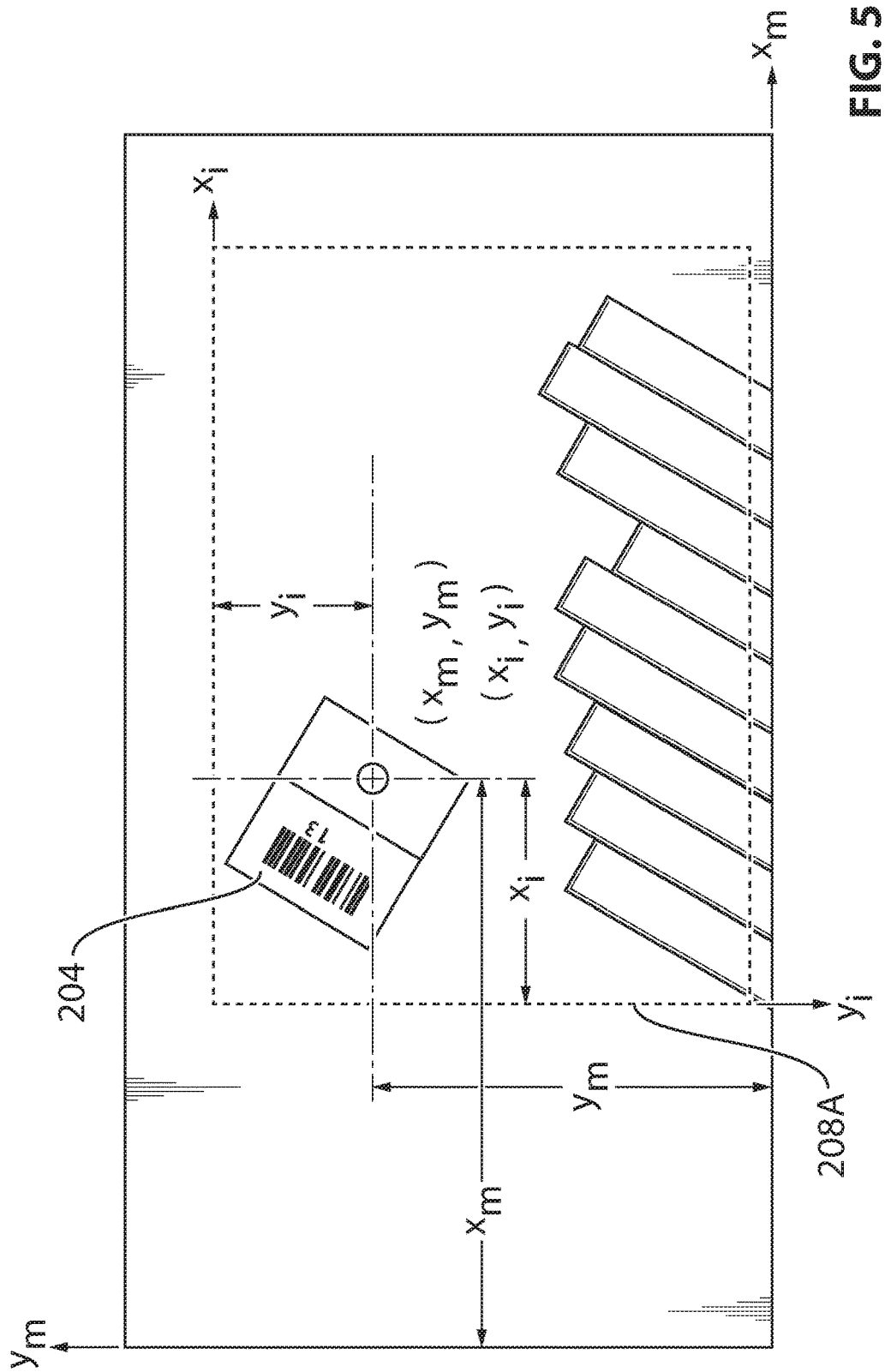

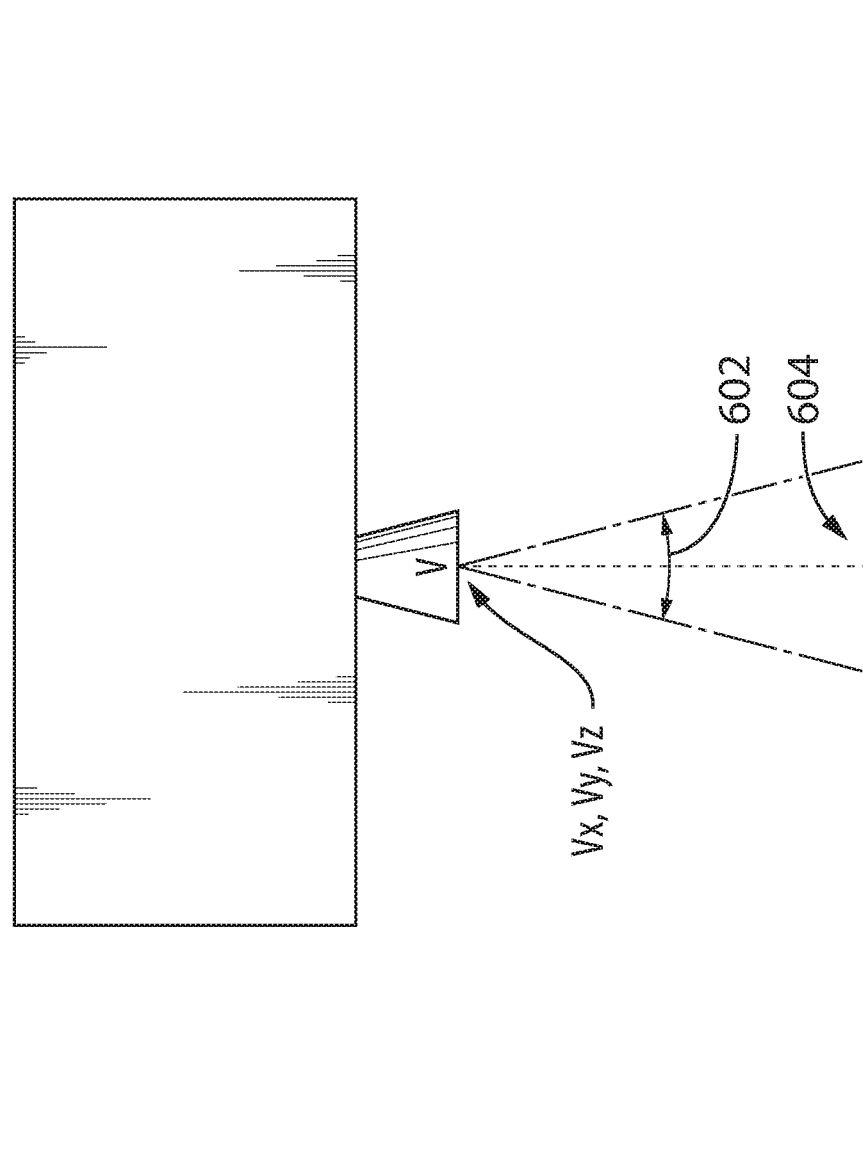

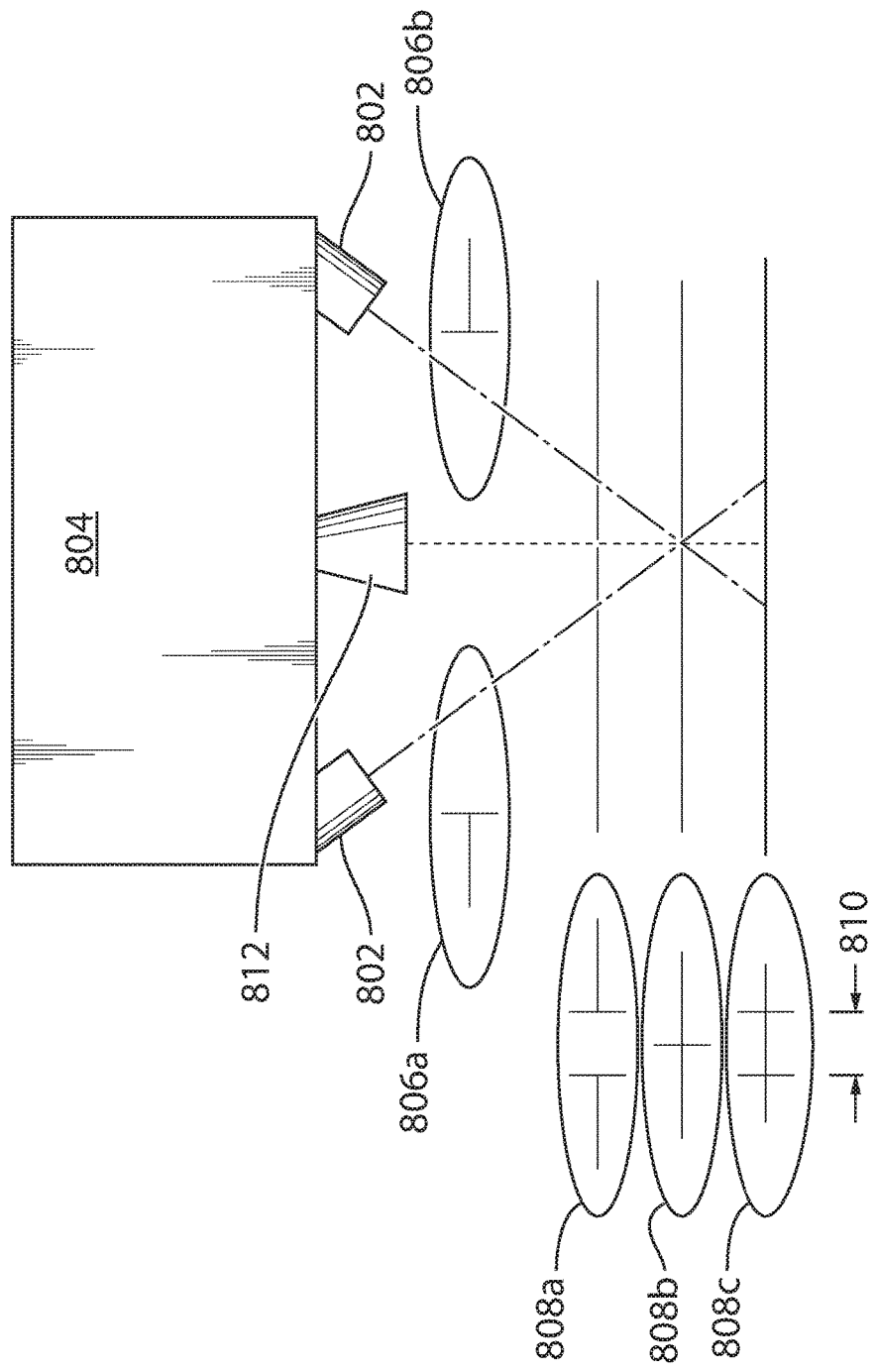

REFERENCE SYSTEM FOR ONLINE VISION INSPECTION

CROSS-REFERENCE TO RELATED APPLICATIONS

This application claims priority under 35 U.S.C. 119(e) to U.S. application No. 62/095,661 filed Dec. 22, 2014, entitled "Reference System For Online Vision Inspection", the entire contents of which are hereby incorporated by reference.

TECHNICAL FIELD

The present invention relates to the field of machine vision inspection and more particularly, to referencing a composite structure within an online vision inspection system.

BACKGROUND OF THE ART

Composite structures (or components) are generally made from two or more constituent materials with significantly different physical or chemical properties. When combined, they produce a structure with characteristics different from the individual materials, with the aim of using the benefit of both.

When manufacturing composite structures using a manufacturing process such as Automated Fiber Placement (AFP) or Automated Tape Layering (ATL), inspecting the dimensional requirements of the manufactured structures is an important part of the manufacturing process.

Known methods for performing dimensional inspection involve gathering data via manual inspection using a handheld probe within a laser tracker system, and comparing the measured data with theoretical data from a Computer-Aided Design (CAD) file. In the case of a composite structure having many plies, manual inspection of the fibers of each ply of the structure is extremely time consuming. Another shortcoming of manual inspection is that it is dependent on the hand and eye skills of the operator, which makes it harder to validate and certify the inspection at a later time, due to the repeatability criteria required for the certification and validation procedure.

Online inspection systems are capable of acquiring images and performing some sort of measurement and/or analysis while a ply is being laid-up. The inspection occurs during manufacturing and does not need to be performed after the lay-up of a ply has been performed. For this to be feasible, the position in space of a point on a ply needs to be accurately known. Online inspection systems having a camera attached to the head of a manufacturing robot tend to rely on robot positioning accuracy, which is known to be poor for performing measurements and for accurately determining a position in space.

Therefore, there is a need to address the issue of referencing the ply in space for automated manufacturing processes.

SUMMARY

There is described a method for referencing a composite structure within an online vision inspection system. Referencing is performed independently from a positioning accuracy of an automated tool with which the composite structure is manufactured. Reference targets provided on a contour of a lay-up surface are used to correlate an image reference system with a mold reference system.

In accordance with a first broad aspect, there is provided a method for referencing a composite structure within a vision inspection system. The composite structure is manufactured by an automated tool on a mold. The method comprises providing at least one reference target on a contour of a lay-up surface; determining an absolute position of the at least one reference target in a mold reference system, the mold reference system setting out an absolute coordinate system for the mold; acquiring an image of the at least one reference target; determining a position of the at least one reference target from the image in an image reference system setting out a measuring coordinate system for pixels in the image; and correlating the mold reference system and the image reference system using the position of the at least one reference target in the mold reference system and the image reference system.

In some embodiments, the method further comprises providing a measuring calibration target within a vision field of an image acquisition device, the measuring calibration target having known dimensions; and acquiring an image of the measuring calibration target and using the known dimensions to determine a size of one pixel in the image. The measuring calibration target may have a plurality of thicknesses to represent a plurality of layers of the composite structure.

In some embodiments, providing at least one reference target comprises providing at least one outer reference target on an outer contour of the mold. The at least one outer reference target may comprise a label having an optical machine-readable representation of identification data. The at least one reference target may have a circular reflective zone. In some embodiments, providing at least one outer reference target comprises providing at least one outer reference target per lay-up band of the composite structure. This may not be the case for ATL, as the vision field may be smaller than a band.

In some embodiments, providing at least one reference target comprises providing at least one inner reference target on a first layer of the composite structure to act as a reference for a second layer of the composite structure on top of the first layer. In some embodiments, the at least one inner reference target may be printed on the first layer. In some embodiments, printing the at least one inner reference target comprises printing an ink marking on the first layer. In some embodiments, printing the at least one inner reference target comprises printing during a lamination of the first layer.

In some embodiments, determining a position of the at least one reference target in a mold reference system comprises laser scanning the at least one reference target.

In some embodiments, acquiring an image of the at least one reference target comprises acquiring the image together with a feature to be inspected. In some embodiments, the method further comprises determining a position of the feature to be inspected.

In accordance with another broad aspect, there is provided a method for referencing a composite structure within a vision inspection system. The composite structure is manufactured by an automated tool on a mold. The method comprises receiving a position of at least one reference target in a mold reference system, the mold reference system setting out an absolute coordinate system for the mold; receiving an image of the at least one reference target; determining a position of the at least one reference target from the image in an image reference system setting out a measuring coordinate system for pixels in the image; and correlating the mold reference system and the image reference system using the position of the at least one reference target in the mold reference system and the image reference system.

In some embodiments, correlating the mold reference system and the image reference system comprises transferring the measuring coordinate system to the absolute coordinate system through angular projection on a theoretical Computer Aided Design (CAD) surface of the mold. Correlating the mold reference system and the image reference system may also comprise calculating tool positioning errors in a flat vision field; applying a correction to measurements in the flat vision field; and transferring corrected measurements into a 3D surface through angular projection. In some embodiments, correlating the mold reference system and the image reference system comprises calculating tool positioning errors in a flat vision field; transferring uncorrected measurements to a 3D surface through angular projection; determining absolute tool positioning errors; and applying a correction to the measurements on the 3D surface using the absolute tool positioning errors.

In some embodiments, the method further comprises correcting a pixel value measurement in accordance with a variation in a vision distance and a vision angle.

In some embodiments, the method further comprises calibrating in real time a vision distance to a surface of the composite structure.

In some embodiments, calibrating in real time comprises stereoscopically projecting a pair of calibration targets onto the composite structure and applying a corrective measure when an image formed by the projected calibration targets differs from a nominal image.

In some embodiments, receiving an image of the at least one reference target comprises receiving an image of the at least one reference target and a feature to be inspected.

In some embodiments, the method further comprises determining a position of the feature to be inspected within the absolute coordinate system of the mold, through use of the image reference system.

In accordance with yet another broad aspect, there is provided a system for referencing a composite structure within a vision inspection system. The composite structure is manufactured by an automated tool on a mold. The system comprises a memory; a processor coupled to the memory; and an application stored in the memory and executable by the processor. The application is configured for receiving a position of at least one reference target in a mold reference system, the mold reference system setting out an absolute coordinate system for the mold; receiving an image of the at least one reference target; determining a position of the at least one reference target from the image in an image reference system setting out a measuring coordinate system for pixels in the image; and correlating the mold reference system and the image reference system using the position of the at least one reference target in the mold reference system and the image reference system.

In some embodiments, correlating the mold reference system and the image reference system comprises transferring the coordinate system for the image to the coordinate system for the mold through angular projection on a theoretical Computer Aided Design (CAD) surface of the mold.

In some embodiments, correlating the mold reference system and the image reference system comprises calculating tool positioning errors in a flat vision field; applying a correction to measurements in the flat vision field; and transferring corrected measurements into a 3D surface through angular projection.

In some embodiments, correlating the mold reference system and the image reference system comprises calculating tool positioning errors in a flat vision field; transferring uncorrected measurements to a 3D surface through angular projection; determining absolute tool positioning errors; and applying a correction to the measurements on the 3D surface using the absolute tool positioning errors.

In some embodiments, the system further comprises correcting a pixel value measurement in accordance with a variation in a vision distance and a vision angle.

In some embodiments, the system further comprises calibrating in real time a vision distance to a surface of the composite structure. In some embodiments, calibrating in real time comprises stereoscopically projecting a pair of calibration targets onto the composite structure and applying a corrective measure when an image formed by the projected calibration targets differs from a nominal image.

In some embodiments, acquiring an image of the at least one reference target comprises acquiring the image together with a feature to be inspected. In some embodiments, the system further comprises determining a position of the feature to be inspected.

In accordance with another broad aspect, there is provided a method for referencing a composite structure within a vision inspection system, the composite structure manufactured by an automated tool on a mold. The method comprises providing at least one reference target on a contour of a lay-up surface; determining an absolute position of the at least one reference target in a mold reference system, the mold reference system setting out an absolute coordinate system for the mold; acquiring an image of the at least one reference target together with a feature under inspection; determining a position of the at least one reference target from the image in an image reference system setting out a measuring coordinate system for pixels in the image; correlating the mold reference system and the image reference system using the position of the at least one reference target in the mold reference system and the image reference system; and determining a position of the feature under inspection.

BRIEF DESCRIPTION OF THE DRAWINGS

Further features and advantages of the present invention will become apparent from the following detailed description, taken in combination with the appended drawings, in which:

FIG. 4a is a top view of an exemplary embodiment of a calibration measuring target;

FIG. 4b is a side view of the calibration measuring target of FIG. 4a;

FIG. 5 is a top view of an exemplary image comprising an outer reference target;

FIG. 6 is a front view of an exemplary image acquisition device;

FIG. 8 is an exemplary embodiment of calibration using stereoscopic projectors;

It will be noted that throughout the appended drawings, like features are identified by like reference numerals.

DETAILED DESCRIPTION

A method and system for referencing a composite structure within a vision inspection system will now be described. For illustrative purposes, the tool used for manufacturing the composite structure is described as an Automated Fiber Placement (AFP) machine but other automated manufacturing tools, such as Automated Tape Layering (ATL) machines, may be used. In order to manufacture a composite structure using AFP, fiber strips (tows) are laid along a mold in multiple layers in order to create a composite structure having the shape of the mold. The fiber strips are placed along the mold in accordance with fiber laying trajectories that are input into the AFP machine to create a given structure in accordance with a set of design parameters. Some of the features that may be inspected include, but are not limited to, fiber gaps, fiber overlap, angle deviations, debris, and tow positions.

The composite structure may comprise various materials, such as but not limited to cements, concrete, reinforced plastics, metal composites and ceramic composites. For example, the composite structure may be composed of composite fiber-reinforced plastics. The composite structure may be used for various applications, including but not limited to buildings, bridges, space crafts, aircrafts, watercrafts, land vehicles including railway vehicles, and structures such as wind turbine blades, swimming pool panels, bathtubs, storage tanks, and counter tops.

The system for online inspection of a composite structure manufactured by an automated tool on a mold generally comprises an image acquisition device. The image acquisition device may be any instrument that records images that can be stored directly, transmitted to another location, or both. For example, the image acquisition device may be a video camera, a still camera, a digital camera, an image sensor, a CCD sensor, a CMOS sensor, an optical fiber sensor, and an active pixel sensor, among other possibilities. Images are processed by an image processor to perform inspection in real time or substantially real time, i.e. as each layer is being laid upon the mold to form the composite structure. The image acquisition device provided in proximity to a head of the automated tool and defines a field of view (FOV) on a surface of the composite structure.

Figure 1:
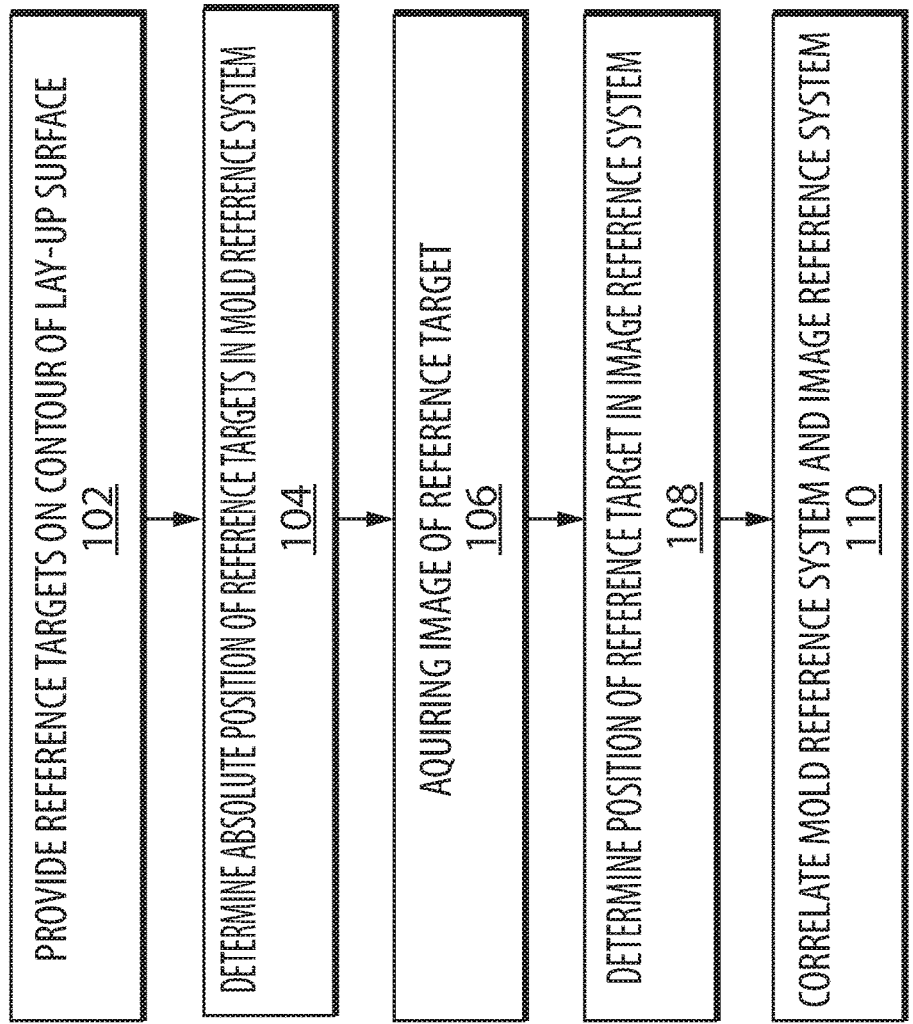
FIG. 1 is a flowchart of an exemplary method for referencing a composite structure within a vision inspection system.

FIG. 1 is a flowchart of an exemplary method for referencing the composite structure within a vision inspection system. As per step 102, reference targets are provided on a contour of a lay-up surface. The reference targets may be outer reference targets provided outside an inspection area and directly on the surface of the mold. The reference targets may also be inner reference targets provided inside an inspection area and directly on a laminate surface.

Figure 2:
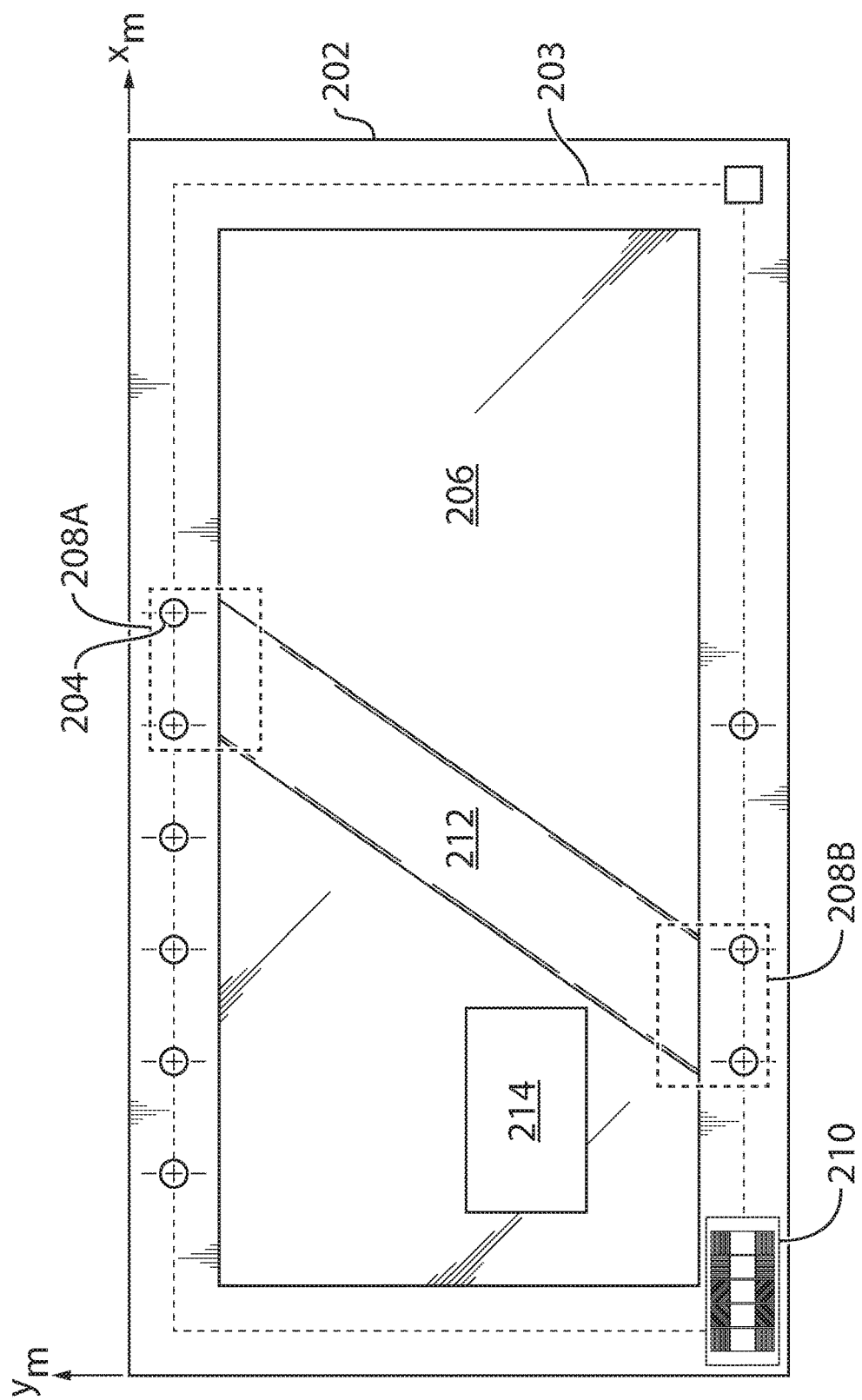
FIG. 2 is a top view of an exemplary embodiment of a mold for manufacturing the composite structure.

FIG. 2 illustrates an exemplary embodiment of the mold 202 on which a composite structure is manufactured using an automated tool. An inspection area 206 comprises a ply made up of bands 212 that extend across the inspection area 206 of the mold 202. Each band 212 is made up of a plurality of tows to form the ply. A mold reference system ($x_m$, $y_m$) defines a set of absolute coordinates for the mold 202. In FIG. 2, the reference targets 204 are outer reference targets positioned along the outer contour of a lay-up surface, such as along the outer contour 203 of the mold 202. As per step 104, the position of each reference target 204 is determined within the mold reference system. An image 208a is acquired, as per step 106, of a reference target 204. The image 208a is defined by an image reference system, which sets out a measuring coordinate system for the pixels in the image 208a. From the image 208a the position of the reference target 204 is determined within the image reference system, as per step 108. The mold reference system is correlated to the image reference system using the known position of the reference target 204 in each reference system, as per step 110. A conversion matrix is thus obtained to go from the image reference system to the mold reference system and vice versa. This method is performed independent of a positioning accuracy of the automated manufacturing tool.

Figure 3B:
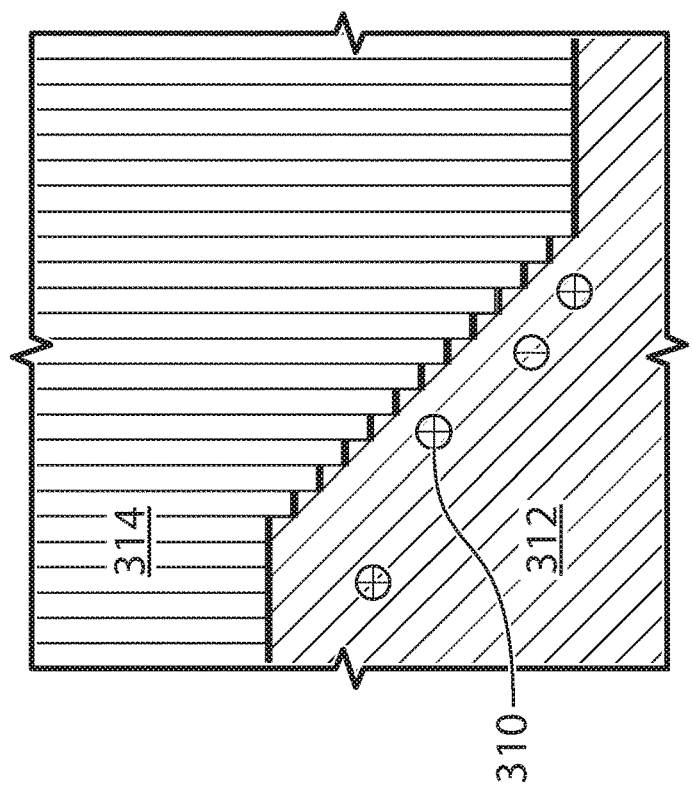
FIG. 3b is an exemplary embodiment of inner reference targets.
Figure 3A:
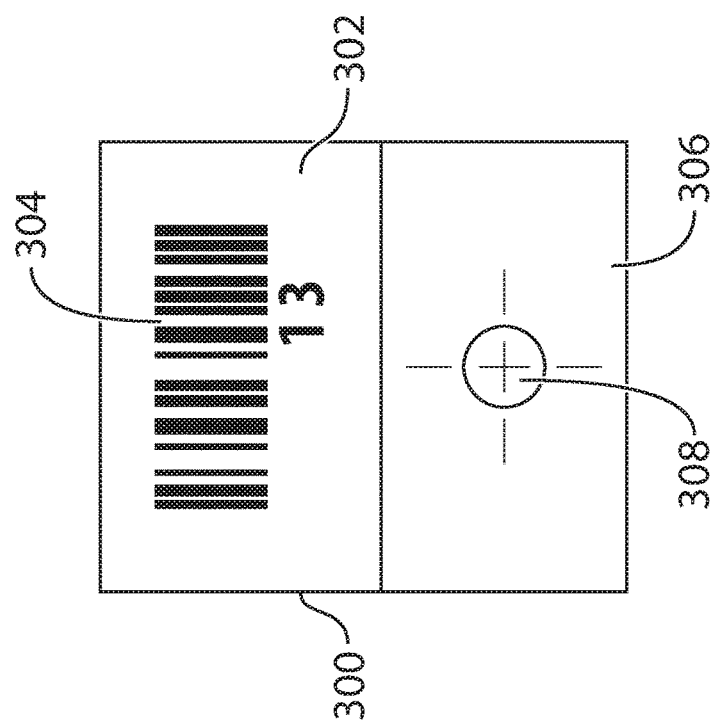
FIG. 3a is an exemplary embodiment of an outer reference target.

FIG. 3a is an exemplary embodiment of an outer reference target 300. In some embodiments, the outer reference targets 300 are labels affixed directly to the mold 202. The labels may be high temperature labels that are constructed of durable materials that won't melt or disintegrate under extreme heat. The labels may comprise optical machine-readable representations 304, such as linear barcodes and matrix barcodes. The optical machine-readable representations 304 may encode identification data for the outer reference targets 300, allowing unique identification of each target. In some embodiments, the outer reference targets 300 are composed of a non-reflective zone 302 comprising the barcode and a reflective zone 306 having a circular mark 308 thereon. One or more laser scanners may be used to scan the outer reference targets 300 to obtain a position within the mold reference system from the circular mark 308. Such scanning may be performed only once at the beginning of the lay-up process, or any time the targets 300 are removed (for example if they are not heat resistant), or each time the mold is removed from its fixture. A barcode reader may be used to obtain a target ID from each outer reference target 300 and a list of targets and their respective locations in the mold reference system may be imported into a database of the image processor. The outer reference targets 300 may take other forms, such as only a reflective zone 306 with the circular mark 308, or a mark of another distinct shape. ID data may be printed directly on the target 300 and read from an image acquisition device. ID data may be provided adjacently to the target 300 instead of directly on it. Alternatively, the outer reference targets 300 may be printed, or otherwise applied, directly on the mold 202, for example by an inkjet printer. Each target 300 may be of a unique shape or size for identifications purposes, instead of providing separate ID data. Other embodiments will be readily understood.

In some embodiments, inner reference targets may also be used. For example, when a ply under inspection has a shorter length than a previous ply, or when there is to be a hole or void in the component being laid-up, lay-up pockets 214 may be created, as illustrated in FIG. 2. The end of a ply under inspection is thus inside the inspection area 206 and does not reach the outer contour 203 of the mold 202. As external features, such as the label-type outer reference targets 204, are not allowed to touch the inspection region 206, inner reference targets are provided inside the inspection area 206. In some embodiments, and as shown in FIG. 3b, inner reference targets 310 are printed directly onto a previous ply 312 for the inspection of a current ply 314. The end of the top ply 314 becomes the lay-up surface and the contour of the lay-up surface is found on the bottom ply 312.

In some embodiments, the inner reference targets 310 are inkjet printed, for example using silver ink. Any non-contact printing process may be used. The printing may be performed during the lay-up of the preceding ply 312. An inkjet printing system may be attached directly to the lay-up head or may be provided separately. The inner reference targets 310 may consist of different shapes, individually recognizable by the image processor, or of a same shape with an accompanying marking for identification purposes. The inner reference targets 310 of FIG. 3b are shown to be circular but other shapes may also be used. Any ink that is compatible with the material of the composite structure may be used.

In some embodiments, a measurement acquired in pixel units by the image acquisition device is converted into physical units, such as inches, centimeters, etc. Correlation of the pixel units to the physical units may be performed using, for example, a measuring calibration target 210. The measuring calibration target 210 may be placed on the outer contour 203 of the mold 202, as illustrated in FIG. 2, or it may be provided separately therefrom, such as on a calibration panel adjacent to the mold 202. FIG. 4a is an exemplary embodiment of the measuring calibration target 210. The measuring calibration target 210 is optionally shown to fit inside a vision field 408 of the image acquisition device, defined by the image reference system $(x_i, y_i)$. The exact dimensions 402 of a measuring zone 404a are known and imported into a memory of the image processor. An image of the measuring calibration target 210 is acquired and the image processor measures the dimension 402 in pixel units. The size of one pixel in physical units may thus be determined.

In some embodiments, a separate measuring zone 404a is provided for each ply of the composite structure. For example, FIG. 4a shows a measuring calibration target 210 for a composite structure having five plies. Measuring calibration targets 210 may be provided for more or less plies. In some embodiments, a fiber direction zone 406 is also provided to represent the direction of the fibers on the composite structure for a given ply.

FIG. 4b is a side view of the measuring calibration target 210. Measuring zones 404B, 404A, 404C, 404D, and 404E correspond to plies 1, 2, 3, 4, and 5, respectively. Each measuring zone 404B, 404A, 404C, 404D, and 404E has a thickness that corresponds to a thickness of the composite structure at each respective ply layer. A vision distance between the image acquisition device and the measuring calibration target 210 is thus set to correspond to the vision distance between the image acquisition device and the surface of the composite structure for each ply, for proper calibration of pixel size. In some embodiments, the measuring calibration target 210 is made from a thin metallic plate of a very low coefficient of thermal expansion material, such as Invar™, Elinvar™, Sital™, Zerodur™, and other low thermal expansion compositions.

In practice, once the mold reference system and image reference system are correlated together, inspection is performed in the inspection area 206 by acquiring a series of images, from a first end of a lay-up band 208b to a second end of the lay-up band 208a, or vice versa. At the end of a lay-up band, the last image will include the outer reference target 204. Once the images are acquired, the image processor may analyze the images and identify, extract (or isolate), and measure the location of a defect or feature under inspection. The image processor may be capable of inspecting multiple defects, each with its own dimensional characteristics, on the same or in successive images. Images may be processed in parallel, such that it is not necessary to wait until the first image is processed to acquire a new image. Defect locations/characteristics are measured and values may be compared with allowable values provided in the memory of the image processor or remotely therefrom, such as in an upper level controller.

FIG. 5 is an exemplary embodiment of the image 208a at the top end of a ply lay-up band. The outer reference target 204 is inside the vision field of the image 208a. The image processor may read the barcode of the target 204 in order to recognize the target 204, thus being able to extract from the list the real coordinates of that target, and may measure the coordinates of the circular reflective area using coordinates in the image reference system $(x_i, y_i)$. Since the coordinates of the target 204 in the mold reference system $(x_m, y_m)$ are known from the preliminary referencing phase, the image processor may use the correlation between the image reference system and the mold reference system to transfer the image coordinates into mold coordinates. The coordinate values of features may be measured in pixels, calculated by the image processor in physical units, and converted into absolute values using the conversion matrix. If the end of band geometry is longer than the vision image size in the direction of the lay-up, successive images may be taken, with a certain overlap, and the conversion matrix may be applied to all successive images. The images should be overlapped enough to allow some common features on consecutive images. The common features may be used to reference the images together.

Note that the mold reference system may be in three dimensions $(x_m, y_m, z_m)$ while the image reference system may be in two dimensions $(x_i, y_i)$. This may be accounted for in various manners. For example, in some embodiments, the outer reference target 204 and/or inner reference target 310 may be used to transfer the image coordinates into the mold coordinates through a theoretical Computer Aided Design (CAD) surface. As per FIG. 6, a vision point V having absolute coordinates $(V_x, V_y, V_z)$ in the mold reference system is determined using the known vision distance and the center of the field of view 604 of known size. The vision point V is based on a theoretical location and orientation of the lay-up head at the moment when the image is acquired. A 2D vision angle 602 is established between the vision point V and the outer edges of the vision field.

Figure 7A:
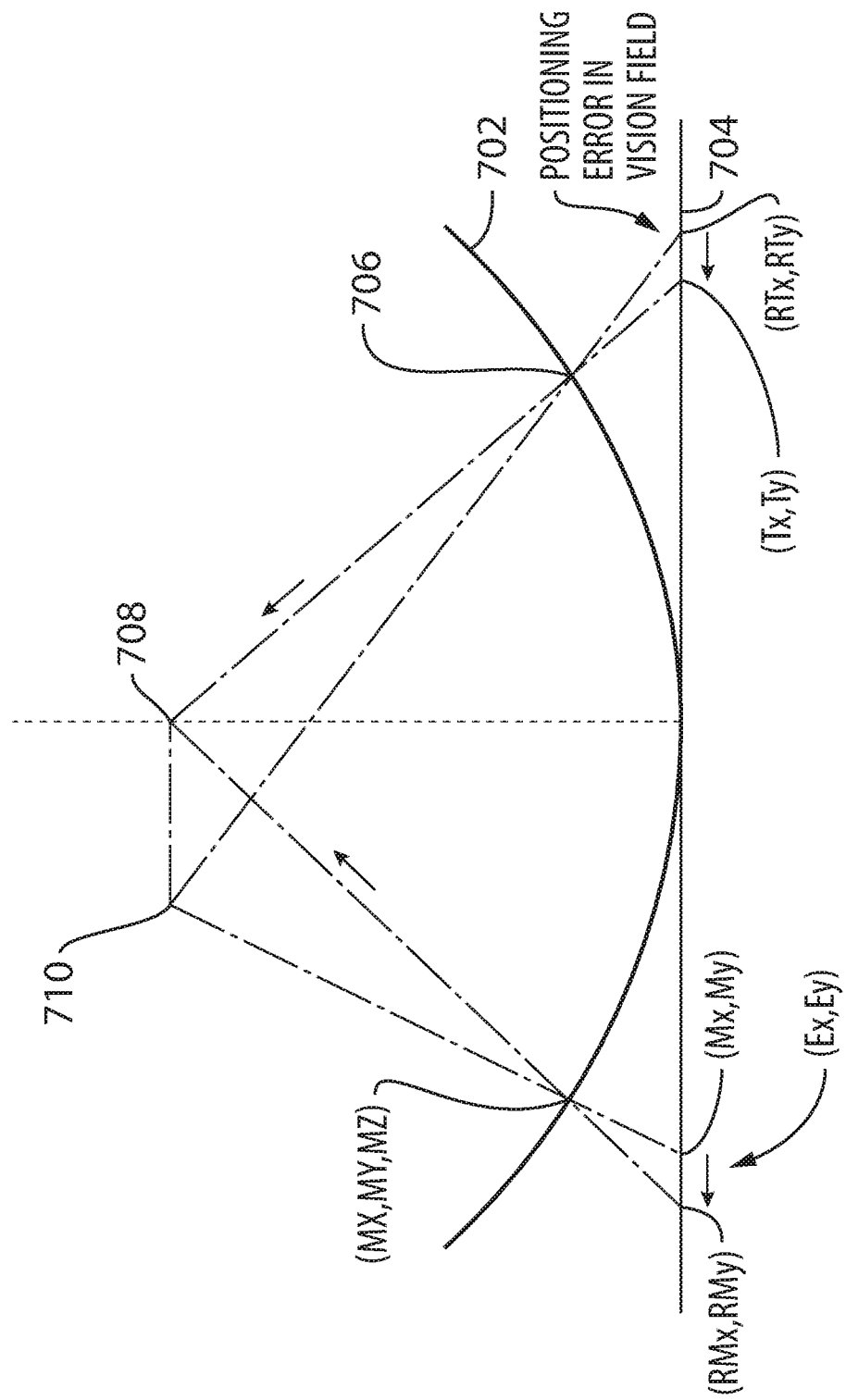
FIG. 7a illustrates a first referencing method for error correction.

FIG. 7a illustrates a pair of projections emerging from the vision point V. FIG. 7a illustrates a position for V theoretical 708, which is known, and a position for V real 710, which is not known. A theoretical 2D curved CAD surface 702 is shown to intersect with the projections of V theoretical 708 and V real 710 at location 706. The vision point V and the 2D curved CAD surface 702 together form a 3D CAD surface. An angular projection of a 2D curved vision field from the CAD surface onto a plane tangent to the CAD surface at the center of the vision field forms a 2D flat vision field 704. The absolute location of the reference target (TX, TY, TZ) is located on the 3D CAD surface. An angular projection of the target location from the CAD surface onto the flat vision field 704 provides the location $(T_x, T_y)$ where the target should be seen in the vision field. The real location of the target in the vision field is measured as ($RT_x$, $RT_y$). A position error ($E_x$, $E_y$) of the automated manufacturing tool is determined in the 2D flat vision field. During inspection, the location of a feature ($M_x$, $M_y$) is measured in the vision field. The real location of the feature in the vision field is determined by applying the correction ($E_x$, $E_y$) to obtain ($RM_x$, $RM_y$). The absolute location (MX, MY, MZ) of the feature is then obtained through angular projection from the 2D vision field onto the CAD surface.

Using this correlation method, tool positioning errors are calculated only in the flat vision field (or tangent plane). Corrections are applied exclusively in the vision field and only then are the results transferred onto the 3D surface. If the curvature of the surface changes significantly between the center of the image and the location of the target, errors may occur. If the curvature difference is small and the vision field is small, the errors are negligible. For example, for a mold having a radius of 20 inches, a vision distance of 8 inches, and a vision field of 4 inches by 2 inches, the in-plane errors on the vision field are 0.0028 inches. For an application where tolerances are much bigger, such as of the order of 0.1 inches, the errors introduced by the measurement technique are acceptable. The errors come from the fact that the tangent plane should be tangent at the point of measurement. The further away the point of measurement is from the center of the image, the bigger the errors will be.

Figure 7B:
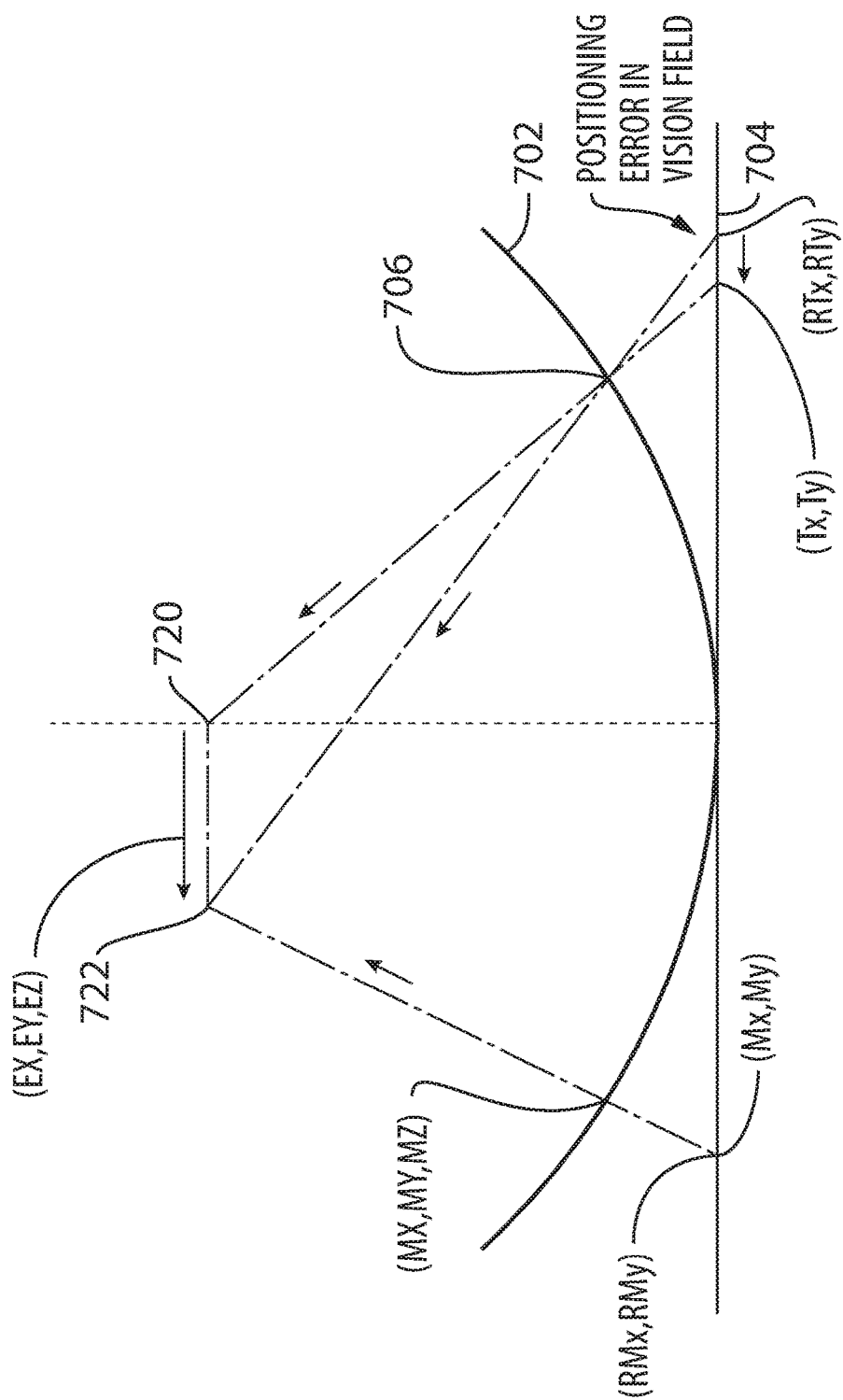
FIG. 7b illustrates a second referencing method for error correction.

In an alternative embodiment, measurements in the image reference system are referenced to the absolute coordinates of a point on the automated manufacturing tool, such as the head. The reference target is used to calculate positioning errors of the automated manufacturing tool. An error correction is applied to an entire set of absolute measurement values. Reference is made to FIG. 7b to illustrate this embodiment. In particular, once the real location ($RT_x$, $RT_y$) of the target in the vision field has been measured, and the position error ($E_x$, $E_y$) of the automated manufacturing tool is determined in the 2D flat vision field, a position error (EX, EY, EZ) is determined in a 3D absolute referencing system under the form of the vision point location. A tool reference system is established using a theoretical location 720 of the tool lay-up head and the location of the vision point V 722. During inspection, the location of a feature ($M_x$, $M_y$) is measured in the vision field. The location of the feature in the mold reference system before corrections is determined ($MR_x$, $MR_y$), and the absolute location of the feature (MX, MY, MZ) is obtained through the application of the lay-up head positioning error correction. Note that the conversion matrix provides a Z coordinate which comes from the CAD file. This Z coordinate does not take into consideration the real location of the feature in the Z axis because the vision field is flat. However, since the system is not inspecting in the Z axis directions, the errors are not relevant.

Using this alternative correlation method, tool positioning errors are calculated in the flat vision field (or tangent plane) and are transferred onto the 3D surface. This method calculates the absolute errors of the tool lay-up head positioning. The same corrections are applied on the 3D surface for all of the measurements, after the measurements are transferred from the 2D vision field onto the 3D surface. If the curvature of the surface changes significantly inside the vision field, the method cannot take the change into consideration. A proper evaluation of the tool positioning error will depend on the distance between the target and the center of the vision field. Measuring features in completely different locations than the location of the target may thus introduce errors in certain cases.

Accuracy of the measurements in the vision field may depend on image size stability. If the distance between the image acquisition device and the composite structure changes, the real dimension of a pixel changes as well. Calibration of the image acquisition device should therefore be repeated whenever the vision distance changes. The vision distance may depend on the deformation of the compaction roller, which may not be perfectly constant. The vision distance may also change when a collision avoidance system of the tool tilts the lay-up head. In such cases, the image processor may apply a correction on the pixel value measurement in accordance with the variation of the vision distance and angle.

In some embodiments, a real time calibration system may be used to continuously measure the real distance from the image acquisition device to the surface of the composite component. An exemplary embodiment of the calibration system is illustrated in FIG. 8. Two distinct projectors 802 are attached to the lay-up head 804 and project onto the surface of the composite component, within the vision field, a calibration target. In this example, the combination of the two calibration targets forms a cross figure. Each projector 802 projects a pattern 806a, 806b, namely a sideways "T", pointing in opposite directions. The projectors 802 are identical but mirror oriented and are positioned such that the vertical line of their projections overlap perfectly at the center of the vision field of the camera 812 when the vision distance is at a nominal value. When the lay-up head 804 moves such that the distance to the surface changes, the image of the combined calibration targets will be modified in accordance with the offset of the lay-up head. For example, a space will be present between the sideways "T's" during an offset where the vision distance is closer than the nominal distance (see 808a), and a dual cross will be projected during an offset where the vision distance is greater than the nominal distance (808c). A nominal distance is illustrated at 808b. In the case of 808a, a negative correction is needed as one pixel has a smaller dimension than another pixel. In the case of 808c, a position correction is needed as one pixel has a greater dimension than another pixel. The vision system can measure the angle and distance in pixels 810 between the two offset vertical lines of the calibration targets and make the correction for the new value of a pixel. This correction may be applied in real time to the measurements, for each new acquired image.

Figure 9:
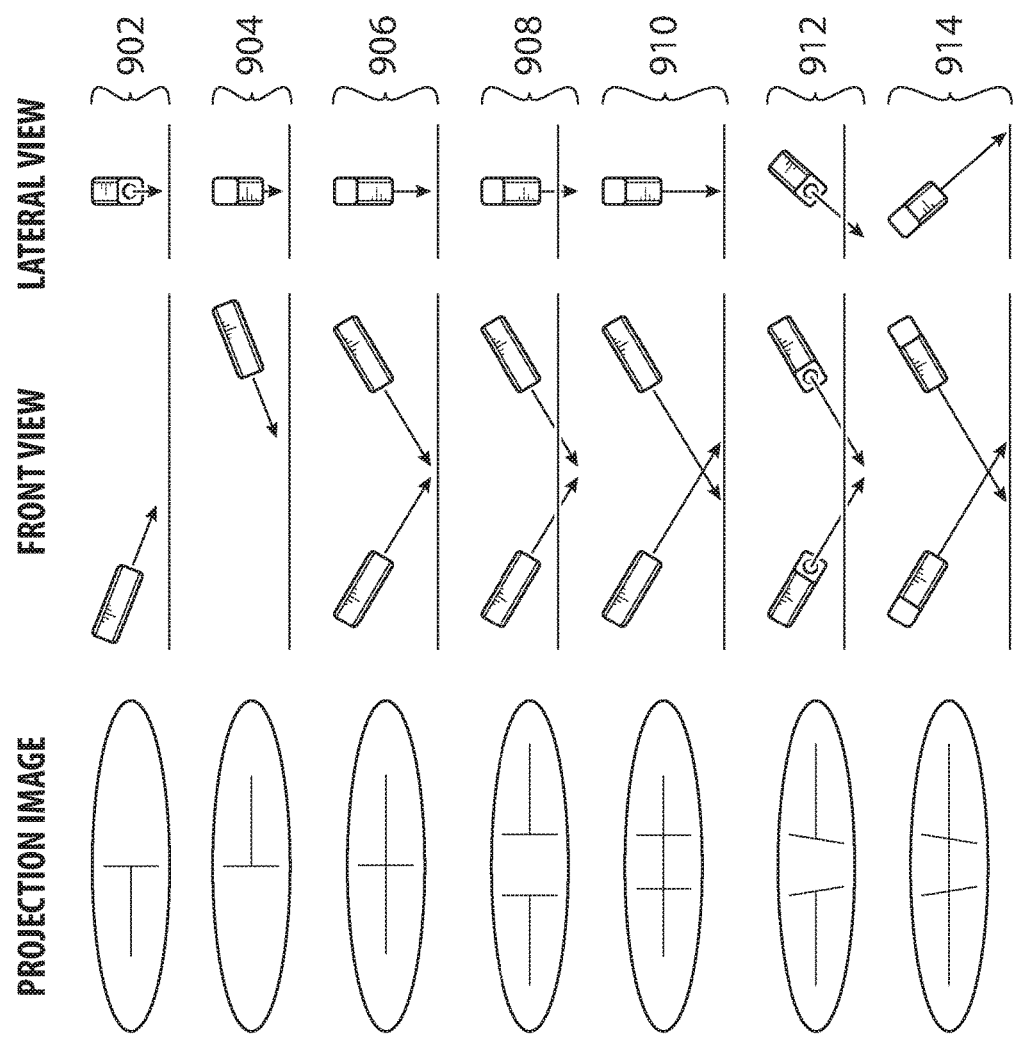
FIG. 9 illustrates possible projections of calibration targets using the embodiment of FIG. 8.

FIG. 9 shows other possible offsets for the two projectors 802, such as when the projectors 802 are tilted forwards or backwards. In some embodiments, the projectors 802 project LED light instead of laser light. As the light is projected on surfaces which might have different fiber orientations, laser light may not be visible if projected in certain directions to the fibers. This issue is not present with LED light. In some embodiments, the projectors 802 use telecentric lenses, which allow them to tilt relative to the surface and still provide an accurate image. The left and right projector images are illustrated at 902 and 904, respectively. The stereoscopic projection image is illustrated at 906. A projection image for projectors 802 closer to the surface is illustrated at 908. A projection image for projectors 802 higher from the surface is illustrated at 910. A closer and forward tilting scenario is illustrated at 912. A further and backward tilted scenario is illustrated at 914.

Figure 10:
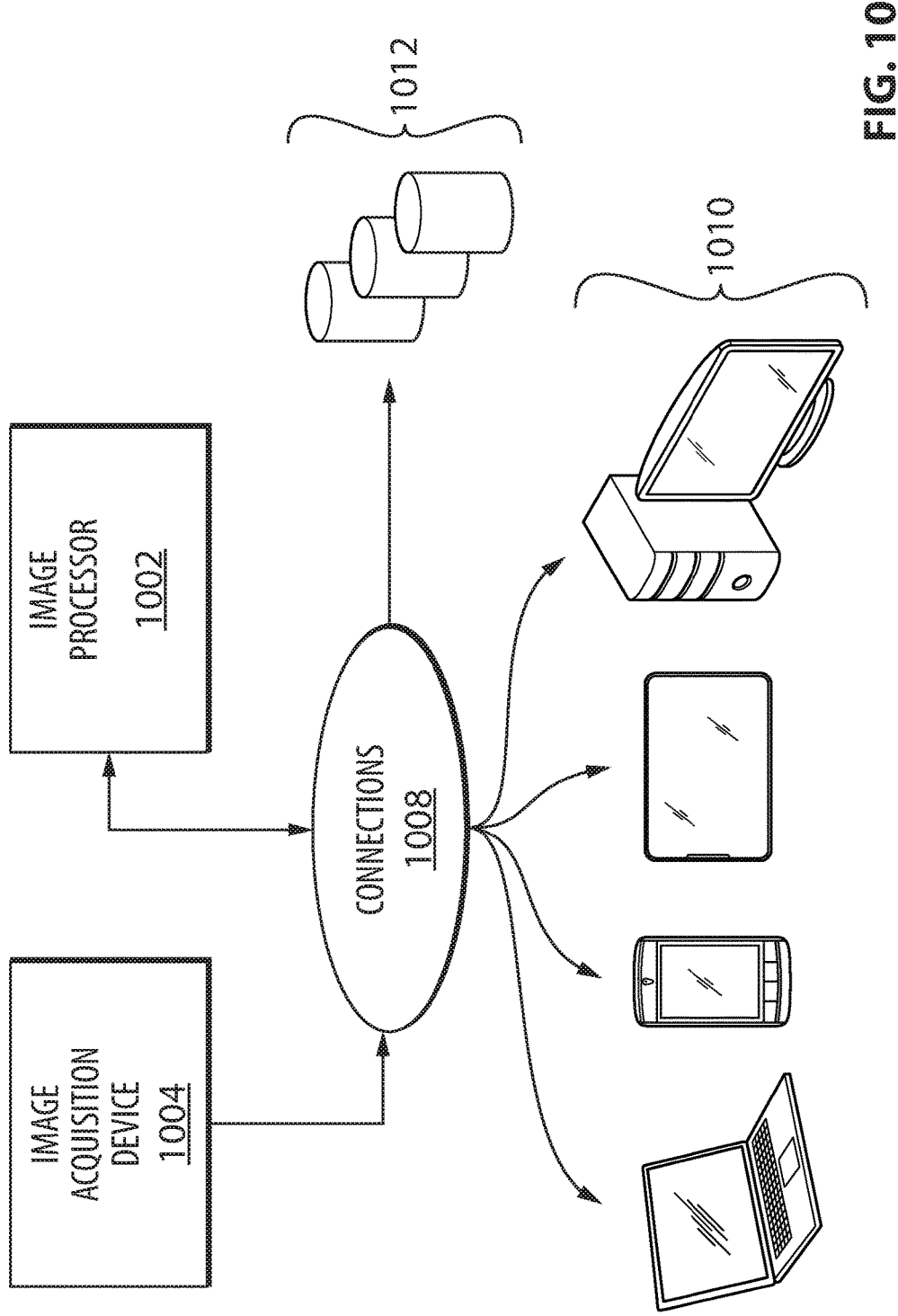
FIG. 10 is an exemplary embodiment of a vision inspection system.
Figure 11:
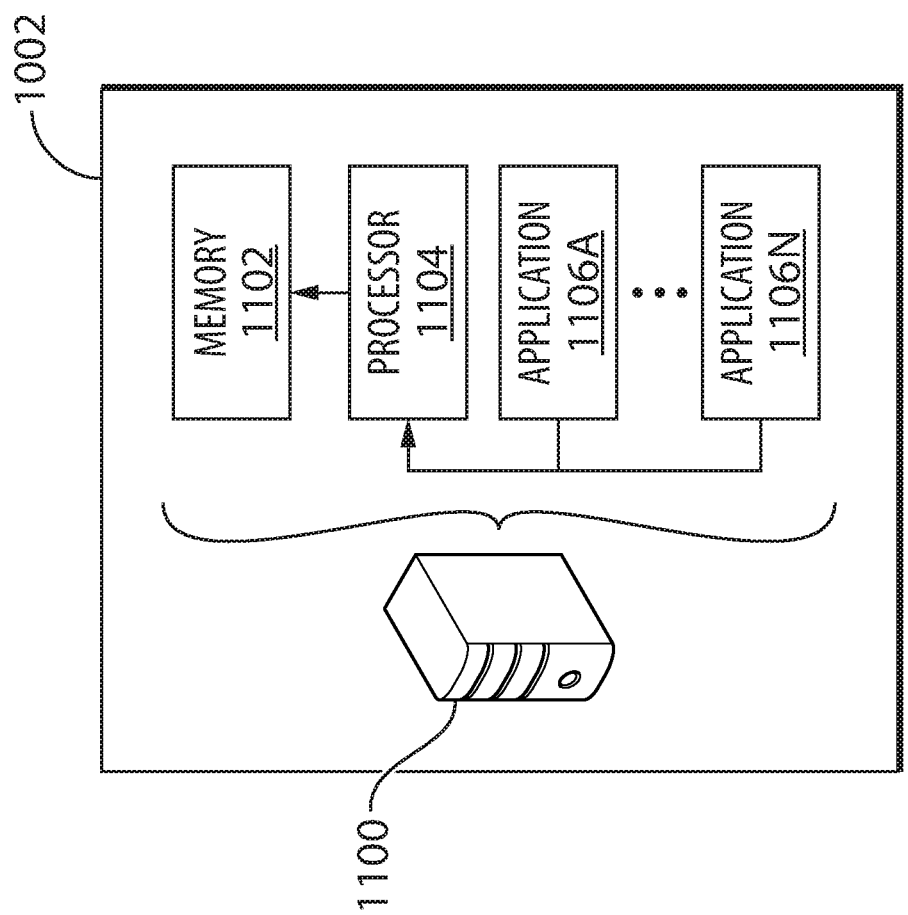
FIG. 11 is an exemplary embodiment of the image processor from the vision inspection system.
Figure 12:
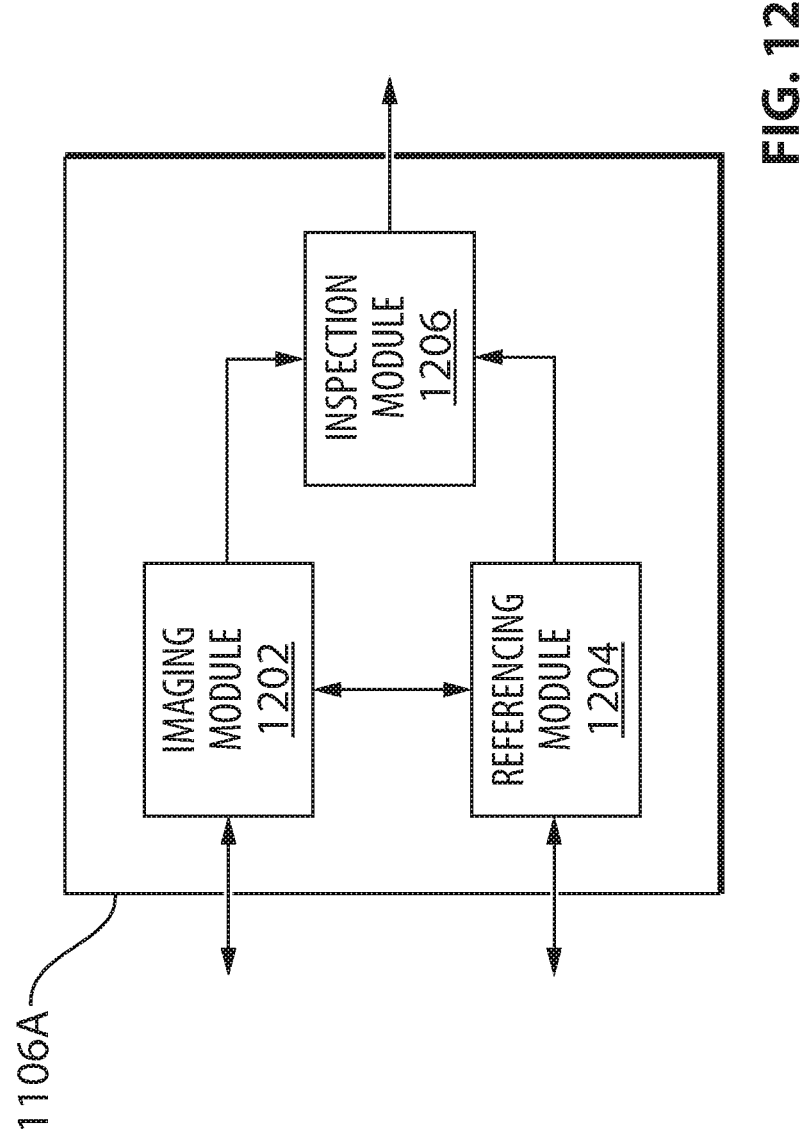
FIG. 12 is an exemplary embodiment of an application running on the image processor.

Referring to FIGS. 10 to 12, a system for referencing a composite structure within a vision inspection system will now be described. In FIG. 10, there is illustrated an image processor 1002 operatively connected to an image acquisition device 1004. The image acquisition device 1004 may be provided separately from or incorporated within the image processor 1002. For example, the image processor 1002 may be integrated with the image acquisition device 1004 either as a downloaded software application, a firmware application, or a combination thereof. The image acquisition device 1004 may be any instrument capable of recording images that can be stored directly, transmitted to another location, or both. These images may be still photographs or moving images such as videos or movies.

Various types of connections 1008 may be provided to allow the image processor 1002 to communicate with the image acquisition device 1004. For example, the connections 1008 may comprise wire-based technology, such as electrical wires or cables, and/or optical fibers. The connections 1008 may also be wireless, such as RF, infrared, Wi-Fi, Bluetooth, and others. Connections 1008 may therefore comprise a network, such as the Internet, the Public Switch Telephone Network (PSTN), a cellular network, or others known to those skilled in the art. Communication over the network may occur using any known communication protocols that enable devices within a computer network to exchange information. Examples of protocols are as follows: IP (Internet Protocol), UDP (User Datagram Protocol), TCP (Transmission Control Protocol), DHCP (Dynamic Host Configuration Protocol), HTTP (Hypertext Transfer Protocol), FTP (File Transfer Protocol), Telnet (Telnet Remote Protocol), SSH (Secure Shell Remote Protocol), and Ethernet. In some embodiments, the connections 1008 may comprise a programmable controller to act as an intermediary between the image processor 1002 and the image acquisition device 1004.

The image processor 1002 may be accessible remotely from any one of a plurality of devices 1010 over connections 1008. The devices 1010 may comprise any device, such as a personal computer, a tablet, a smart phone, or the like, which is configured to communicate over the connections 1008. In some embodiments, the image processor 1002 may itself be provided directly on one of the devices 1010, either as a downloaded software application, a firmware application, or a combination thereof. Similarly, the image acquisition device 1004 may be integrated with one of the device 1010. In some embodiments, the image acquisition device 1004 and the image processor 1002 are both provided directly on one of devices 1010, either as a downloaded software application, a firmware application, or a combination thereof.

One or more databases 1012 may be integrated directly into the image processor 1002 or any one of the devices 1010, or may be provided separately therefrom (as illustrated). In the case of a remote access to the databases 1012, access may occur via connections 1008 taking the form of any type of network, as indicated above. The various databases 1012 described herein may be provided as collections of data or information organized for rapid search and retrieval by a computer. The databases 1012 may be structured to facilitate storage, retrieval, modification, and deletion of data in conjunction with various data-processing operations. The databases 1012 may be any organization of data on a data storage medium, such as one or more servers or long term data storage devices. The databases 1012 illustratively have stored therein any one of acquired images, position data of outer reference targets, position data of inner reference targets, identification data of outer reference targets, identification data of inner reference targets, conversion matrix, pixel unit values, physical unit values, CAD surface data, vision point data, vision distance data, vision angle data, and calibration targets data.

As shown in FIG. 11, the image processor 1002 illustratively comprises one or more server(s) 1100. For example, a series of servers corresponding to a web server, an application server, and a database server may be used. These servers are all represented by server 1100 in FIG. 11. The server 1100 may be accessed by a user, such as a technician or an assembly line worker, using one of the devices 1010, or directly on the system 1002 via a graphical user interface. The server 1100 may comprise, amongst other things, a plurality of applications 1106a . . . 1106n running on a processor 1104 coupled to a memory 1102. It should be understood that while the applications 1106a . . . 1106n presented herein are illustrated and described as separate entities, they may be combined or separated in a variety of ways.

The memory 1102 accessible by the processor 1104 may receive and store data. The memory 1102 may be a main memory, such as a high speed Random Access Memory (RAM), or an auxiliary storage unit, such as a hard disk, a floppy disk, or a magnetic tape drive. The memory 1102 may be any other type of memory, such as a Read-Only Memory (ROM), or optical storage media such as a videodisc and a compact disc. The processor 1104 may access the memory 1102 to retrieve data. The processor 1104 may be any device that can perform operations on data. Examples are a central processing unit (CPU), a front-end processor, a microprocessor, and a network processor. The applications 1106a . . . 1106n are coupled to the processor 1104 and configured to perform various tasks. An output may be transmitted to the image acquisition device 1004 and/or to the devices 1010.

FIG. 12 is an exemplary embodiment of an application 1106a running on the processor 1104. The application 1106a illustratively comprises an imaging module 1202, a referencing module 1204, and an inspection module 1206. The imaging module 1202 is configured to receive images acquired by the image acquisition device 1004. It may also be configured to control the image acquisition device 1004, i.e. output control signals for acquiring the images and positioning the field of view. The imaging module 1202 may transfer to the referencing module 1204 images used for referencing the composite structure within the vision inspection system. For example, the imaging module 1202 is configured to receive an image of at least one outer reference target and provide it to the referencing module 1204. The referencing module 1204 is configured to receive a position of the at least one outer reference target in the mold reference system, and determine the position of the at least one outer reference target in the image reference system. The referencing module 1204 may also be configured to correlate the mold reference system and the image reference system and obtain the conversion matrix. The referencing module 1204 provides the conversion matrix to the inspection module 1206 for inspecting features on the composite structure. The inspection module 1206 receives images acquired and from the imaging module 1202 for the inspection.

The inspection module 1206 may be configured to inspect the features of the composite structure in real time by analyzing the images and identifying, extracting, and measuring the locations of features to be inspected. Multiple features may be inspected on the same or in successive images concurrently. Feature locations/characteristics are measured and values are compared with allowable values provided in the memory 1102 or in the remote databases 1012. A Go/No Go decision may be made automatically by the inspection module 1206. Inspection reports may be generated with deviation data. Manufacturing may be interrupted for repairing defects and restarted once the repair is complete.

In some embodiments, the referencing module 1204 is configured to correlate the mold reference system with the image reference system through the CAD surface, as described above. For example, in one embodiment, the referencing module 1204 is configured to calculate tool positioning errors in a flat vision field, apply a correction to measurements in the flat vision field, and transfer the corrected measurements into a 3D surface. In another embodiment, the reference module 1204 is configured to calculate the tool positioning errors in the flat vision field, transfer uncorrected measurements to the 3D surface, and apply a correction to the measurements on the 3D surface.

In some embodiments, the referencing module 1204 is configured to correct a pixel value measurement in accordance with a variation in a vision distance and a vision angle of the image acquisition device 1004. This may comprise calibrating in real time the vision distance to the surface of the composite structure using the stereoscopic projectors described above. Images comprising the calibration targets may be acquired by the image acquisition device 1004, received by the imaging module 1202, and provided to the referencing module 1204 for processing.

The referencing module 1204 may also be configured to output control signals to the imaging module 1202 and/or to the image acquisition device 1004. For example, the referencing module 1204 may request a new image of the measuring calibration target when the vision distance is found to vary beyond the nominal. This new image is used to recalibrate the physical dimension of one pixel unit. Similarly, the referencing module 1204 may be configured to output control signals to an inkjet printer for providing inner reference targets on a ply for referencing a subsequent ply that does not reach the outer contour of the mold. The referencing module 1204 may then analyze images comprising the inner reference targets for referencing purposes. Identification data and/or absolute coordinates of inner and outer reference targets may be input to the image processor 1002 and stored in the memory 1102 for later access by the referencing module 1204. Dimensions of the measuring calibration target may also be input to the image processor 1002 and stored in the memory 1102 for later access by the referencing module 1204.

The referencing module 1204 is thus configured to allow inspection of the features of the composite structure to be performed independently of a positioning accuracy of the manufacturing tool. The outer reference targets placed on the mold surface outside of the inspection area do not need to be provided at a precise location and/or orientation as they are recognizable, identifiable, and measurable by the referencing module 1204. In some embodiments, a measuring calibration target is used to determine the dimension of a pixel in physical units. In addition, stereoscopic projection of calibration targets may be used to compensate for variations of the vision distance depth and angle and to establish the right value of a pixel for each image collected by the image acquisition device.

The above description is meant to be exemplary only, and one skilled in the relevant arts will recognize that changes may be made to the embodiments described without departing from the scope of the invention disclosed. For example, the blocks and/or operations in the flowcharts and drawings described herein are for purposes of example only. There may be many variations to these blocks and/or operations without departing from the teachings of the present disclosure. For instance, the blocks may be performed in a differing order, or blocks may be added, deleted, or modified. While illustrated in the block diagrams as groups of discrete components communicating with each other via distinct data signal connections, it will be understood by those skilled in the art that the present embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present embodiment. The present disclosure may be embodied in other specific forms without departing from the subject matter of the claims. Also, one skilled in the relevant arts will appreciate that while the systems, methods and computer readable mediums disclosed and shown herein may comprise a specific number of elements/components, the systems, methods and computer readable mediums may be modified to include additional or fewer of such elements/components. The present disclosure is also intended to cover and embrace all suitable changes in technology. Modifications which fall within the scope of the present invention will be apparent to those skilled in the art, in light of a review of this disclosure, and such modifications are intended to fall within the appended claims.

The invention claimed is:

1. A method for referencing a composite structure within a vision inspection system, the composite structure manufactured by an automated tool on a mold, the method comprising:
providing at least one reference target on a contour of a lay-up surface;
determining an absolute position of the at least one reference target in a mold reference system, the mold reference system setting out an absolute coordinate system for the mold;
acquiring an image of the at least one reference target;
determining a position of the at least one reference target from the image in an image reference system setting out a measuring coordinate system for pixels in the image;
correlating the mold reference system and the image reference system using the position of the at least one reference target in the mold reference system and the image reference system;
providing a measuring calibration target within a vision field of an image acquisition device, the measuring calibration target having known dimensions; and
acquiring an image of the measuring calibration target and using the known dimensions to determine a size of one pixel in the image, wherein the measuring calibration target has a plurality of thicknesses to represent a plurality of layers of the composite structure.

2. The method of claim 1, wherein providing at least one reference target comprises providing at least one outer reference target on an outer contour of the mold.

3. The method of claim 2, wherein the at least one outer reference target comprises a label having an optical machine-readable representation of identification data.

4. The method of claim 2, wherein providing at least one outer reference target comprises providing the at least one reference target with a circular reflective zone.

5. The method of claim 1, wherein providing at least one reference target comprises providing at least one inner reference target on a first layer of the composite structure to act as a reference for a second layer of the composite structure on top of the first layer.

6. The method of claim 5, wherein providing at least one inner reference target comprises printing the at least one inner reference target on the first layer.

7. The method of claim 6, wherein printing the at least one inner reference target comprises printing an ink marking on the first layer.

8. The method of claim 6, wherein printing the at least one inner reference target comprises printing during a lamination of the first layer.

9. The method of claim 1, wherein determining a position of the at least one reference target in the mold reference system comprises laser scanning the at least one reference target.

10. The method of claim 1, wherein providing at least one reference target comprises providing at least one reference target per lay-up band of the composite structure.

11. The method of claim 1, wherein acquiring an image of the at least one reference target comprises acquiring the image together with a feature to be inspected.

12. The method of claim 11, further comprising determining a position of the feature to be inspected within the absolute coordinate system of the mold, through use of the image reference system.

13. A method for referencing a composite structure within a vision inspection system, the composite structure manufactured by an automated tool on a mold, the method comprising:
    receiving a position of at least one reference target in a mold reference system, the mold reference system setting out an absolute coordinate system for the mold;
    receiving an image of the at least one reference target;
    determining a position of the at least one reference target from the image in an image reference system setting out a measuring coordinate system for pixels in the image;
    correlating the mold reference system and the image reference system using the position of the at least one reference target in the mold reference system and the image reference system;
    providing a measuring calibration target within a vision field of an image acquisition device, the measuring calibration target having known dimensions; and
    acquiring an image of the measuring calibration target and using the known dimensions to determine a size of one pixel in the image, wherein the measuring calibration target has a plurality of thicknesses to represent a plurality of layers of the composite structure.

14. The method of claim 13, wherein correlating the mold reference system and the image reference system comprises transferring the measuring coordinate system to the absolute coordinate system through angular projection on a theoretical Computer Aided Design (CAD) surface of the mold.

15. The method of claim 13, wherein correlating the mold reference system and the image reference system comprises:
    calculating tool positioning errors in a flat vision field;
    applying a correction to measurements in the flat vision field; and
    transferring corrected measurements into a 3D surface through angular projection.

16. The method of claim 13, wherein correlating the mold reference system and the image reference system comprises:
    calculating tool positioning errors in a flat vision field;
    transferring uncorrected measurements to a 3D surface through angular projection;
    determining absolute tool positioning errors; and
    applying a correction to the measurements on the 3D surface using the absolute tool positioning errors.

17. The method of claim 13, further comprising correcting a pixel value measurement in accordance with a variation in a vision distance and a vision angle.

18. The method of claim 13, further comprising calibrating in real time a vision distance to a surface of the composite structure.

19. The method of claim 18, wherein calibrating in real time comprises stereoscopically projecting a pair of calibration targets onto the composite structure and applying a corrective measure when an image formed by the projected calibration targets differs from a nominal image.

20. The method claim 13, wherein receiving an image of the at least one reference target comprises receiving an image of the at least one reference target and a feature to be inspected.

21. The method of claim 20, further comprising determining a position of the feature to be inspected within the absolute coordinate system of the mold, through use of the image reference system.

22. A system for referencing a composite structure within a vision inspection system, the composite structure manufactured by an automated tool on a mold, the system comprising:
    a memory;
    a processor coupled to the memory; and
    an application stored in the memory and executable by the processor for:
        receiving a position of at least one reference target in a mold reference system, the mold reference system setting out an absolute coordinate system for the mold;
        receiving an image of the at least one reference target;
        determining a position of the at least one reference target from the image in an image reference system setting out a measuring coordinate system for pixels in the image;
        correlating the mold reference system and the image reference system using the position of the at least one reference target in the mold reference system and the image reference system;
        providing a measuring calibration target within a vision field of an image acquisition device, the measuring calibration target having known dimensions; and
        acquiring an image of the measuring calibration target and using the known dimensions to determine a size of one pixel in the image, wherein the measuring calibration target has a plurality of thicknesses to represent a plurality of layers of the composite structure.

23. The system of claim 22, wherein correlating the mold reference system and the image reference system comprises transferring the measuring coordinate system to the absolute coordinate system through angular projection on a theoretical Computer Aided Design (CAD) surface of the mold.

24. The system of claim 22, wherein correlating the mold reference system and the image reference system comprises:
    calculating tool positioning errors in a flat vision field;
    applying a correction to measurements in the flat vision field; and
    transferring corrected measurements into a 3D surface through angular projection.

25. The system of claim 22, wherein correlating the mold reference system and the image reference system comprises:
    calculating tool positioning errors in a flat vision field;
    transferring the tool positioning errors to a 3D surface;

transferring uncorrected measurements to the 3D surface through angular projection;

determining absolute tool positioning errors; and applying a correction to the measurements on the 3D surface using the absolute tool positioning errors.

26. The system claim 22, wherein the application is further configured for correcting a pixel value measurement in accordance with a variation in a vision distance and a vision angle.

27. The system of claim 22, wherein the application is further configured for calibrating in real time a vision distance to a surface of the composite structure.

28. The system of claim 27, wherein calibrating in real time comprises stereoscopically projecting a pair of calibration targets onto the composite structure and applying a corrective measure when an image formed by the projected calibration targets differs from a nominal image.

29. A method for referencing a composite structure within a vision inspection system, the composite structure manufactured by an automated tool on a mold, the method comprising:

providing at least one reference target on a contour of a lay-up surface;

determining an absolute position of the at least one reference target in a mold reference system, the mold reference system setting out an absolute coordinate system for the mold;

acquiring an image of the at least one reference target together with a feature under inspection;

determining a position of the at least one reference target from the image in an image reference system setting out a measuring coordinate system for pixels in the image;

correlating the mold reference system and the image reference system using the position of the at least one reference target in the mold reference system and the image reference system;

determining a position of the feature under inspection within the absolute coordinate system of the mold through use of the image reference system;

providing a measuring calibration target within a vision field of an image acquisition device, the measuring calibration target having known dimensions; and acquiring an image of the measuring calibration target and using the known dimensions to determine a size of one pixel in the image, wherein the measuring calibration target has a plurality of thicknesses to represent a plurality of layers of the composite structure.

30. The method of claim 29, wherein determining a position of the feature is performed while the automated tool is laying-up the composite structure.

31. A system for inspecting a feature of a composite structure manufactured by an automated fiber placement (AFP) tool, the AFP tool laying fiber tows on a mold in order to create multiple lay-up surfaces that form the composite structure, the system comprising:

a memory;

a processor coupled to the memory; and an application stored in the memory and executable by the processor for:

receiving a position of at least one reference target in a mold reference system, the reference target being located on a contour of a lay-up surface, the mold reference system setting out an absolute coordinate system for the mold;

receiving an image of the at least one reference target together with the feature of the composite structure under inspection;

determining a position of the at least one reference target from the image in an image reference system setting out a measuring coordinate system for pixels in the image;

correlating the mold reference system and the image reference system using the position of the at least one reference target in the mold reference system and the image reference system; and determining a position of the feature under inspection within the absolute coordinate system of the mold through use of the image reference system.

\* \* \* \* \*